US009383320B2

(12) United States Patent
Naito et al.

(10) Patent No.: US 9,383,320 B2
(45) Date of Patent: Jul. 5, 2016

(54) CELL ANALYZER

(71) Applicant: SYSMEX CORPORATION, Kobe-shi, Hyogo (JP)

(72) Inventors: Takamichi Naito, Kobe (JP); Takeo Saitou, Kobe (JP)

(73) Assignee: SYSMEX CORPORATION, Kobe-shi (JP)

( * ) Notice: Subject to any disclaimer, the term of this patent is extended or adjusted under 35 U.S.C. 154(b) by 0 days.

(21) Appl. No.: 14/141,211

(22) Filed: Dec. 26, 2013

(65) Prior Publication Data
US 2014/0154793 A1    Jun. 5, 2014

Related U.S. Application Data

(63) Continuation of application No. PCT/JP2012/066291, filed on Jun. 26, 2012.

(30) Foreign Application Priority Data

Jun. 27, 2011 (JP) .................... 2011-141500

(51) Int. Cl.
G01N 33/00 (2006.01)
G01N 21/64 (2006.01)
G01N 15/14 (2006.01)

(52) U.S. Cl.
CPC .......... *G01N 21/6486* (2013.01); *G01N 15/147* (2013.01); *G01N 15/1429* (2013.01); *G01N 15/1475* (2013.01); *G01N 2015/1472* (2013.01); *G01N 2015/1488* (2013.01); *G01N 2015/1497* (2013.01)

(58) Field of Classification Search
CPC .......... G01N 21/6486; G01N 15/1429; G01N 2015/1488
See application file for complete search history.

(56) References Cited

U.S. PATENT DOCUMENTS 6,169,816 B1    1/2001  Ravkin
2006/0204071 A1  9/2006  Ortyn et al.
2007/0178067 A1  8/2007  Maier et al.

(Continued)

FOREIGN PATENT DOCUMENTS

CN    102053057 A    5/2011
EP    2327977 A2    6/2011
JP    3-018704 A    1/1991

(Continued)

OTHER PUBLICATIONS

International Search Report of PCT/JP2012/066291 dated Sep. 25, 2012.

*Primary Examiner* — Sam P Siefke
(74) *Attorney, Agent, or Firm* — Mots Law, PLLC

(57) ABSTRACT

A cell analyzer includes a flow cell through which a sample containing a cell flows; an imaging unit that captures the cell contained in the sample flowing through the flow cell; a cell image storage unit that stores a cell image captured by the imaging unit; a light source that irradiates the sample flowing through the flow cell with light; a light receiving unit that receives light from the cell irradiated with the light from the light source and outputs a signal corresponding to a light receiving amount; a waveform data storage unit that stores data indicating change in the light receiving amount obtained based on the output signal; a display unit; and a control unit that controls the display unit to display the cell image and a graph representing a waveform of data for the cell in the cell image and/or a marker corresponding to the data.

17 Claims, 15 Drawing Sheets

(56) References Cited

U.S. PATENT DOCUMENTS

| | | |
|---|---|---|
| 2008/0108103 A1 | 5/2008 | Ishisaka et al. |
| 2010/0196917 A1 | 8/2010 | Ishisaka et al. |
| 2011/0104744 A1 | 5/2011 | Ozasa et al. |

FOREIGN PATENT DOCUMENTS

| | | |
|---|---|---|
| JP | 2008-092920 A | 4/2008 |
| JP | 2010-167067 A | 8/2010 |

(a)

(b)

(a)

(b)

(a)

(b)

(a)

(b)

CELL ANALYZER

TECHNICAL FIELD

The present invention relates to a cell analyzer.

BACKGROUND ART

There is known a cell analyzer that flows a sample containing cells through a flow cell, irradiates the sample with light, receives the light from the cells irradiated with light, and analyzes the cells based on change in a light receiving amount by the passing of the cells.

As such a cell analyzer, there is also known a cell analyzer equipped with a camera for capturing a cell contained in the sample flowing through the flow cell (refer to, U.S. Patent Application Publication No. 2008/108103, for example). In the cell analyzer described in U.S. Patent Application Publication No. 2008/108103, the image data obtained by capturing the cell is stored in an image storage unit, and is output from an output unit as necessary.

The cell analyzer described in U.S. Patent Application Publication No. 2008/108103 discriminates cancerous/atypical cells from a plurality of cells using characteristic parameters calculated by analyzing waveform data based on the change in the light receiving amount, but the cells come in various shapes and sizes and include cells that cannot be appropriately analyzed with only the analysis based on the light receiving amount.

In such a case, visual analysis by the operator becomes necessary. In the cell analyzer described in U.S. Patent Application Publication No. 2008/108103, the image data of the cell stored in the image storage unit can be output from the output unit. However, even if only the image data is output, it may be difficult for the operator to analyze the cell in the image data because the contour of the cell in the image data is blurred, or the position of the nucleus of the cell cannot be determined.

SUMMARY OF THE INVENTION

The scope of the present invention is defined solely by the appended claims, and is not affected to any degree by the statements within this summary.

A first aspect of the present invention is a cell analyzer comprising:
 a flow cell through which a sample containing a cell flows;
 an imaging unit that captures the cell contained in the sample flowing through the flow cell;
 a cell image storage unit that stores a cell image captured by the imaging unit;
 a light source that irradiates the sample flowing through the flow cell with light;
 a light receiving unit that receives light from the cell irradiated with the light from the light source and outputs a signal corresponding to a light receiving amount;
 a waveform data storage unit that stores data indicating change in the light receiving amount obtained based on the output signal;
 a display unit; and
 a control unit that controls the display unit to display the cell image and a graph representing a waveform of data for the cell in the cell image and/or a marker corresponding to the data.

EMBODIMENTS OF THE INVENTION

An embodiment of a cell analyzer of the present invention will be described in detail below with reference to the accompanying drawings.

[Overall Configuration of Cell Analyzer]

Figure 1:
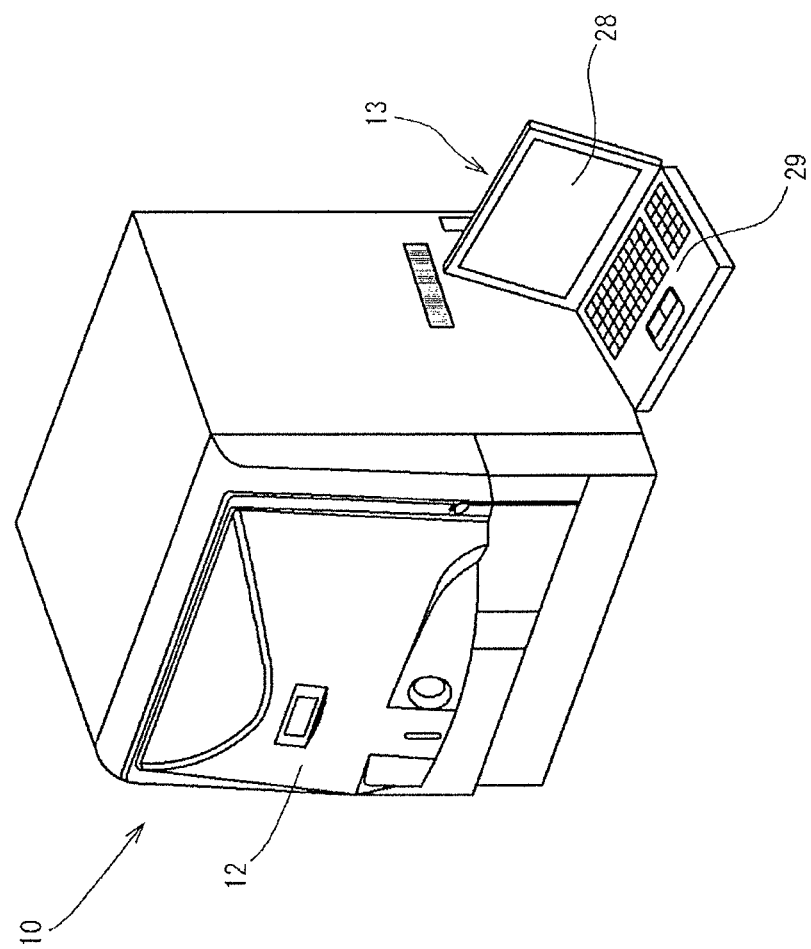
FIG. 1 is a perspective explanatory view of a cell analyzer according to one embodiment of the present invention.

FIG. 1 is a perspective explanatory view of a cell analyzer 10 according to one embodiment of the present invention. The cell analyzer 10 is used to determine whether or not the cells include cancerous cells and atypical cells (hereinafter, also referred to as "abnormal cells") by flowing a measurement sample including epidermal cells of a uterine cervix collected from a patient through a flow cell, irradiating the measurement sample flowing through the flow cell with laser light, and detecting/analyzing light (forward scattered light, side fluorescence, etc.) from the measurement sample. Specifically, the cell analyzer is used to screen the uterine cervix cancer using the epidermal cells of the uterine cervix. The cell analyzer 10 includes an apparatus main body 12 for performing measurement of the sample, and the like, and a system control unit 13, connected to the apparatus main body 12, for performing analysis of the measurement result, and the like.

Figure 2:
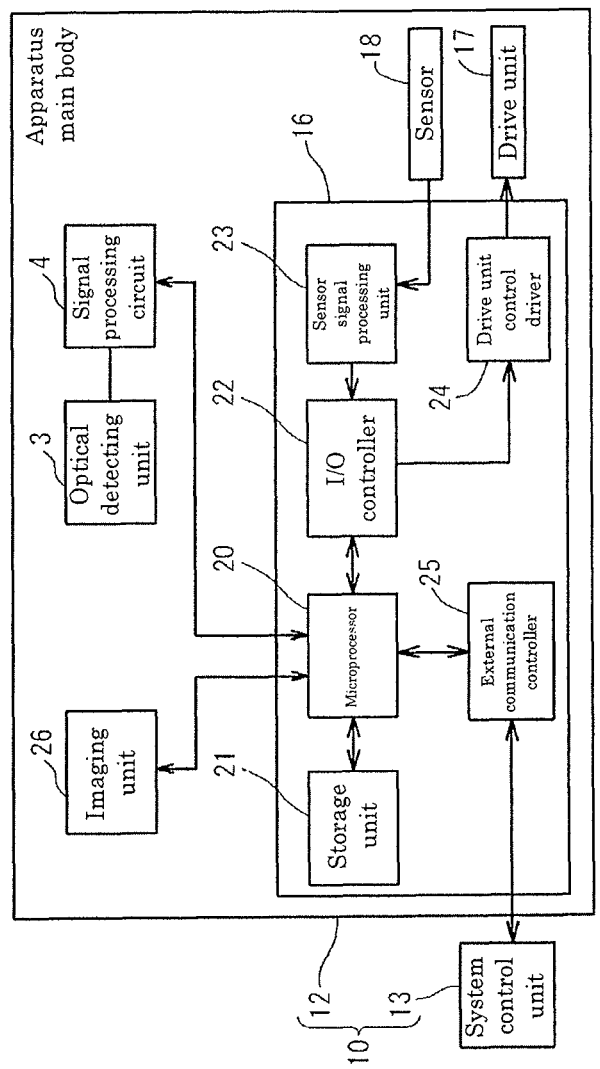
FIG. 2 is a block diagram showing a configuration of the cell analyzer shown in FIG. 1.

As shown in FIG. 2, the apparatus main body 12 of the cell analyzer 10 includes: an optical detecting unit 3 for detecting information on the size of the cell and the nucleus, and the like from the measurement sample; a signal processing circuit 4; a measurement control unit 16; a drive unit 17 such as a motor, an actuator, and a valve; various types of sensors 18; and an imaging unit 26 for capturing the image of the cell. The signal processing circuit 4 includes: an analog signal processing circuit for performing amplification process, filtering process, and the like on the amplified output, in which the output of the optical detecting unit 3 is amplified with a pre-amplifier (not shown); an A/D converter for converting the output of the analog signal processing circuit to a digital signal; and a digital signal processing circuit for performing a predetermined waveform process on the digital signal. The measurement control unit 16 controls the operation of the drive unit 17 while processing the signal of the sensor 18, so that the measurement sample can be aspirated and measured. When screening the uterine cervix cancer, a sample prepared by performing known processing such as centrifuge (condensation), dilution, stirring, and PI staining on the cell (epidermal cell) collected from the uterine cervix of the patient (subject) can be used for the measurement sample. The prepared measurement sample is contained in a test tube and installed at a position on a lower side of a pipette (not shown) of the apparatus main body 12, so that the measurement sample is aspirated with the pipette and supplied to the flow cell along with the sheath solution, whereby the sample flow is formed in the flow cell. The PI staining is carried out with propidium iodide (PI), which is a fluorescence stain fluid containing pigments. In the PI staining, the staining is selectively performed on the nucleus, so that fluorescence from the nucleus can be detected.

[Configuration of Measurement Control Unit]

The measurement control unit 16 includes a microprocessor 20, a storage unit 21, an I/O controller 22, a sensor signal processing unit 23, a drive unit control driver 24, an external communication controller 25, and the like. The storage unit 21 includes a ROM, a RAM, and the like, where control programs for controlling the drive unit 17 and data necessary for the execution of the control program are stored in the ROM. The microprocessor 20 can load the control program in the RAM or directly execute the control program from the ROM.

The signal from the sensor 18 is transmitted to the microprocessor 20 through the sensor signal processing unit 23 and the I/O controller 22. The microprocessor 20 can control the drive unit 17 through the I/O controller 22 and the drive unit control driver 24 in response to the signal from the sensor 18 by executing the control program.

The data processed by the microprocessor 20 and the data necessary for the processing of the microprocessor 20 are transmitted and received with an external device such as the system control unit 13 via the external communication controller 25.

[Configuration of System Control Unit]

Figure 3:
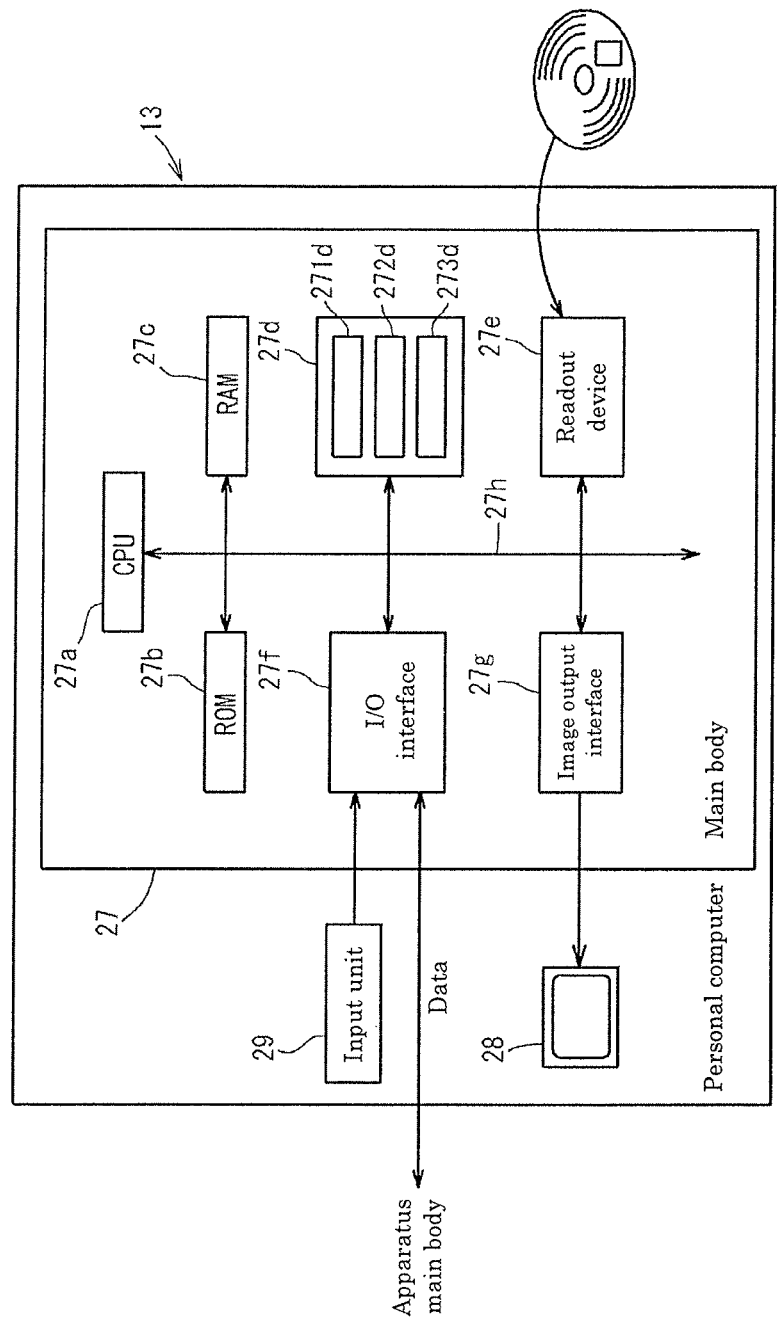
FIG. 3 is a block diagram of a personal computer configuring a system control unit in the cell analyzer shown in FIG. 1.

FIG. 3 is a block diagram of the system control unit 13. The system control unit 13 includes a personal computer, and the like, and is mainly configured by a main body 27, a display unit 28, and an input unit 29. The main body 27 is mainly configured by a CPU 27a, a ROM 27b, a RAM 27c, a hard disk 27d, a readout device 27e, an I/O interface 27f, and an image output interface 27g. Such elements are communicably connected by a bus 27h.

The CPU 27a can execute computer programs stored in the ROM 27b and the computer programs loaded in the RAM 27c. The ROM 27b is configured by mask ROM, PROM, EPROM, EEPROM, and the like, and is recorded with computer programs to be executed by the CPU 27a, data used for the same, and the like. The RAM 27c is configured by SRAM, DRAM, or the like. The RAM 27c is used to read out the computer programs recorded on the ROM 27b and the hard disk 27d. Upon executing the computer programs, the RAM 27c is used as a work region of the CPU 27a.

The hard disk 27d is installed with various computer programs 273d to be executed by the CPU 27a such as an operating system and an application program, as well as data used in the execution of the computer programs. The hard disk 27d is installed with an operating system which provides a graphical user interface environment, for example, Windows (registered trademark) manufactured and sold by US Microsoft Corp. The hard disk 27d also includes a waveform data storage unit 271d for storing the waveform data, to be described later, and a cell image storage unit 272d for storing the cell image, to be described later.

The hard disk 27d is also installed with an operation program for performing transmission of measurement order (operation command) to the measurement control unit 16 of the cell analyzer 10, reception and processing of measurement results measured by the apparatus main body 12, display of the processed analysis results, and the like. Such operation program is assumed to operate on the operating system.

The readout device 27e is configured by a flexible disk drive, a CD-ROM drive, a DVD-ROM drive, or the like, and can read out the computer program or the data recorded in a portable recording media. The I/O interface 27f is configured by a serial interface such as USB, IEEE 1394, and RS-232C; a parallel interface such as SCSI, IDE, and IEEE 1284; and an analog interface including D/A converter and A/D converter. The input unit 29 including a keyboard and a mouse is connected to the I/O interface 27f, so that data can be input to the personal computer when the user operates the input unit 29. The I/O interface 27f is connected to the apparatus main body 12 to be able to transmit and receive data and the like with the apparatus main body 12.

The image output interface 27g is connected to the display unit 28 configured by LCD, CRT, or the like to output an image signal corresponding to the image data and a waveform signal corresponding to the waveform data provided from the CPU 27a to the display unit 28. The display unit 28 displays an image (screen) in accordance with the input image signal and waveform signal.

[Configuration of Optical Detecting Unit and Imaging Unit]

Figure 4:
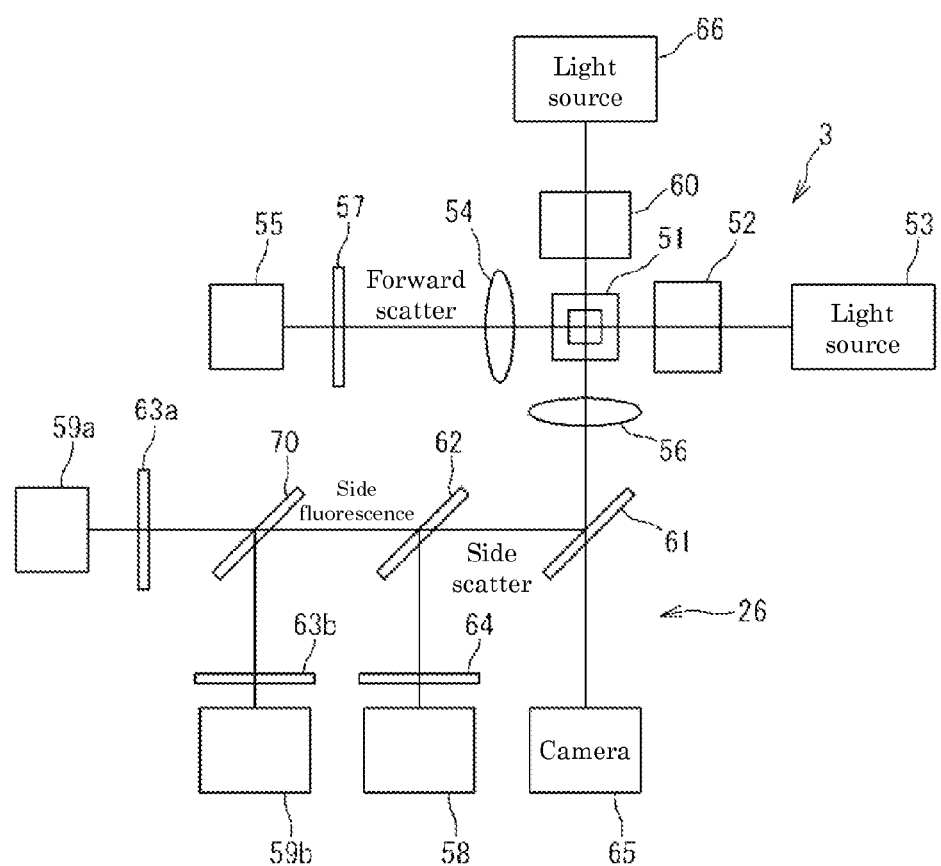
FIG. 4 is a block diagram showing a configuration of an optical detecting unit in the cell analyzer shown in FIG. 1.

FIG. 4 is a view showing the configuration of the optical detecting unit 3 and the imaging unit 26. The optical detecting unit 3 is equipped with a light source 53 including a semiconductor laser, where the laser light radiated from the light source 53 is collected on the measurement sample flowing through the flow cell 51 via a lens system 52. The forward scattered light generated from the cells in the measurement sample by the laser light is detected by a photodiode (light receiving unit) 55 via an objective lens 54 and a filter 57. The lens system 52 is configured by a lens group including a collimator lens, cylinder lens, condenser lens, and the like.

Furthermore, the side fluorescence and the side scattered light generated from the cells enter a dichroic mirror 61 via an objective lens 56 arranged at the side of the flow cell 51. The side fluorescence and the side scattered light reflected by the dichroic mirror 61 enter a dichroic mirror 62. In the present embodiment, double staining using red dye and green dye is carried out to stain the nucleus of the cell.

The side fluorescence transmitted through the dichroic mirror 62 further enters a dichroic mirror 70 and is divided to a red fluorescence and a green fluorescence, where the red fluorescence transmitted through the dichroic mirror 70 is detected by a photo-multiplier 59a via a filter 63a, and the green fluorescence reflected by the dichroic mirror 70 is detected by a photo-multiplier 59b via a filter 63b. The side scattered light reflected by the dichroic mirror 62 is detected by a photo-multiplier 58 via a filter 64.

The photodiode 55, the photo-multiplier 58, the photo-multiplier 59a, and the photo-multiplier 59b convert the detected light to electric signals, and output a forward scattered light signal, a side scattered light signal, a side red fluorescence signal, and a side green fluorescence signal, respectively. Such signals are amplified by a pre-amplifier (not shown) and transmitted to the signal processing circuit 4 (see FIG. 2) described earlier.

Signal processing such as A/D conversion processing and filter processing is performed on each of the above signals in the signal processing circuit 4, and the waveform data such as forward scattered light data (FSC), side scattered light data (SSC), side red fluorescence data (SRFL), and side green fluorescence data (SGFL), and characteristic parameters, to be described later, reflecting the characteristics of such waveform data are transmitted to the system control unit 13 described above through the external communication controller 25 and stored in the hard disk 27d by the microprocessor 20. Each waveform data of the forward scattered light data (FSC), the side scattered light data (SSC), the side red fluorescence data (SRFL), and the side green fluorescence data (SGFL) stored in the hard disk 27d is the data in which a numerical value indicating the intensity of the forward scattered light, the side scattered light, the side red fluorescence, and the side green fluorescence from the cell when the cell passes through a predetermined detection region in the flow cell irradiated with laser is collected at a constant time interval. That is, each waveform data of the forward scattered light data (FSC), the side scattered light data (SSC), the side red fluorescence data (SRFL), and the side green fluorescence data (SGFL) stored in the hard disk 27d is the data indicating temporal change in the intensity of the detected light.

A gas laser may be used for the light source 53 in place of the semiconductor laser, but it is preferable to adopt the semiconductor laser in terms of low cost, compactness, and low power consumption. The manufacturing cost can be reduced, and furthermore, the apparatus can be miniaturized and the power can be saved by adopting the semiconductor laser. In the present embodiment, a blue semiconductor laser having short wavelength that is advantageous in narrowing the beam is used. The blue semiconductor laser is also effective with respect to a fluorescence excitation wavelength of the PI and the like. Among the semiconductor lasers, a red semiconductor laser, which is of low cost and long lifespan, and which can be stably supplied from the manufacturing company, may also be used.

In the present embodiment, the imaging unit 26 is arranged in addition to the optical detecting unit 3. As shown in FIG. 4, the imaging unit 26 is equipped with a light source 66 including a pulse laser and a CCD camera 65, where the laser light from the pulse laser 66 enters the flow cell 51 via a lens system 60, and further transmits through the objective lens 56 and the dichroic mirror 61 to form an image on the camera 65. The pulse laser 66 emits light at a timing determined on the basis of the characteristic parameters, as will be described later, to enable capturing by the camera 65.

As shown in FIG. 2, the image of the cell captured by the camera 65 is transmitted to the system control unit 13 through the external communication controller 25 by the microprocessor 20. The image of the cell is stored in the cell image storage unit 272d of the hard disk 27d in correspondence with the characteristic parameters obtained on the basis of the forward scattered light data (FSC), the side scattered light data (SSC), and the side red fluorescence data (SRFL) of the cell shown in the image in the system control unit 13.

[Content of Characteristic Parameters]

In the present embodiment, various characteristic parameters reflecting the characteristics of the forward scattered light data (FSC), the side scattered light data (SSC), and the side red fluorescence data (SRFL) are acquired through the signal processing by the signal processing circuit 4, and the cells can be analyzed using the characteristic parameters. The representative characteristic parameters will be described below.

<Characteristic Parameters to Use for Analysis>

In the present embodiment, the signal processing circuit 4 performs signal processing on the forward scattered light signal output from the photodiode 55 to obtain the forward scattered light data. The signal processing circuit 4 acquires, for a plurality of characteristic parameters reflecting the size of the particle, the signal waveform pulse width of the forward scattered light (FSCW) generated from the obtained forward scattered light data, and the signal waveform peak value of the forward scattered light (FSCP). Furthermore, in the present embodiment, the signal processing circuit 4 performs signal processing on the side red fluorescence signal output from the photo-multiplier 59a to obtain the side red fluorescence data. The signal processing circuit 4 acquires, for a plurality of characteristic parameters reflecting the DNA amount of the cell, the area of the red fluorescence (RFLA) generated from the obtained side red fluorescence data, and the signal waveform peak value of the side red fluorescence. The signal waveform pulse width of the forward scattered light (FSCW), the signal waveform peak value of the forward scattered light (FSCP), the area of the red fluorescence (RFLA), and the signal waveform peak value of the red fluorescence will be described later.

Figure 5:
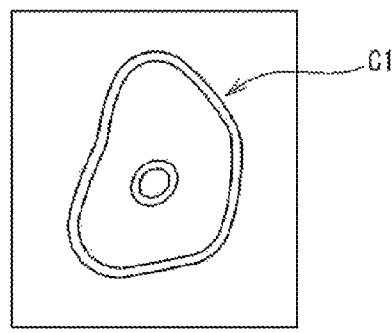
FIG. 5 is a view showing a signal waveform of a single cell.
Figure 5:
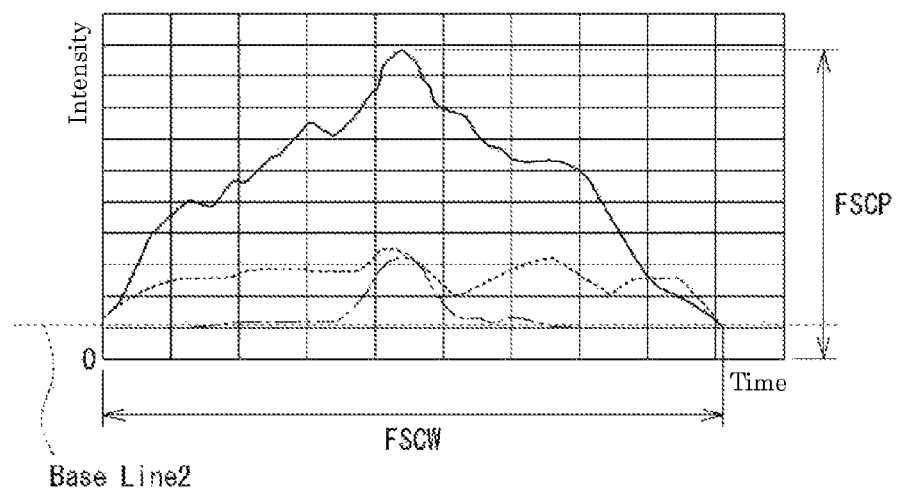

FIG. 5(a) is an explanatory view of a single cell (non-aggregated cell) C1, and FIG. 5(b) is a view showing a signal waveform of the cell C1. As shown in FIG. 5(b), the signal waveform peak value of the forward scattered light (FSCP) represents the maximum intensity (FSCP in the figure) of the detected forward scattered light. The signal waveform pulse width of the forward scattered light (FSCW) represents the signal waveform width of the forward scattered light having a larger intensity than the base line (Base Line 2).

The signal waveform peak value of the red fluorescence represents the maximum intensity of the detected red fluorescence. The area (fluorescence amount) of the pulse of the fluorescence signal of the red fluorescence (RFLA) represents the area of the portion surrounded by the base line and the fluorescence signal waveform. The signal processing circuit 4 acquires the area (fluorescence amount) of the pulse of the red fluorescence signal (RFLA), which is the value reflecting the DNA amount of the nucleus of the cell to be analyzed, as the characteristic parameter from the red fluorescence light signal output from the photo-multiplier 59a.

[Cell Analyzing Process]

Figure 6:
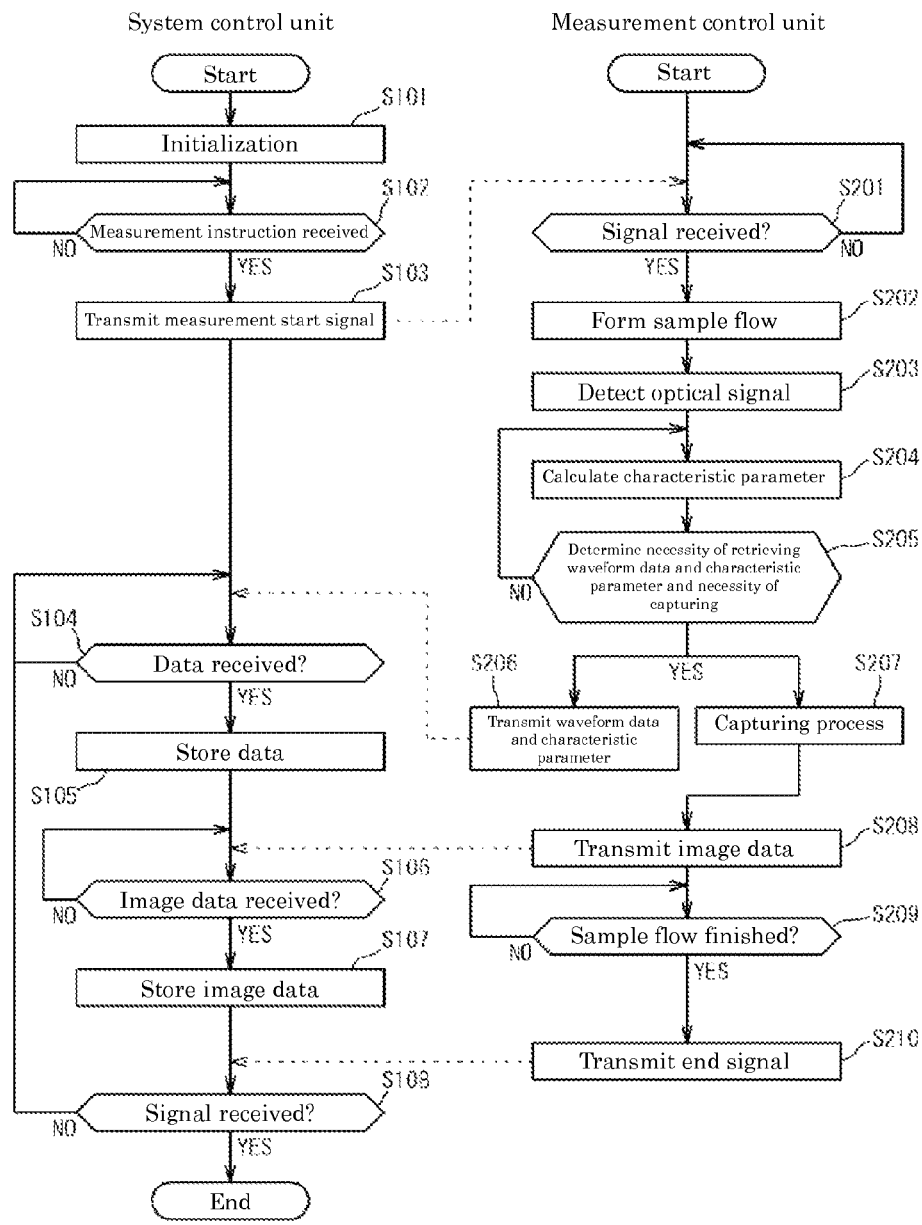
FIG. 6 is a flowchart showing one example of a flow of a cell analyzing process.

The control of the CPU 27a of the system control unit 13 and the microprocessor 20 of the apparatus main body 12 executed in the cell analysis process using the cell analyzer according to the present embodiment will now be described with reference to FIG. 6.

When the power of the system control unit 13 is turned ON, the CPU 27a of the system control unit 13 performs initialization of the computer program stored in the system control unit 13 (step S101). The CPU 27a then determines whether or not a measurement instruction from a user (operator) is received (step S102), and transmits a measurement start signal to the apparatus main body 12 through the I/O interface 27f (step S103) if the measurement instruction is received (YES).

When the measurement start signal transmitted from the system control unit 13 is received by the microprocessor 20 of the apparatus main body 12 (step S201), the measurement sample accommodated in the test tube is aspirated by the pipette and supplied to the flow cell 51 shown in FIG. 4, and the microprocessor 20 controls the operation of the drive unit 17 while processing the signal from the sensor 18 so that the sample flow is formed (step S202) in the apparatus main body 12. The microprocessor 20 controls the optical detecting unit 3 such that the cell in the measurement sample flowing through the flow cell 51 is irradiated with the laser light, and the forward scattered light from the cell is detected by the photodiode 55, the side scattered light is detected by the photo-multiplier 58, the side red fluorescence is detected by the photo-multiplier 59a, and the side green fluorescence is detected by the photo-multiplier 59b (step S203).

The forward scattered light signal, the side scattered light signal, and the fluorescence signal output from the optical detecting unit 3 are transmitted to the signal processing circuit 4. The microprocessor 20 acquires the forward scattered light data (FSC), the side scattered light data (SSC), and the side fluorescence data (SFL) obtained by performing a predetermined processing in the signal processing circuit 4, temporarily stores the same in the storage unit 21 of the apparatus main body 12 serving as a waveform storage buffer, to be described later, and acquires the characteristic parameters described above (the signal waveform pulse width of the forward scattered light, the signal waveform peak value of the forward scattered light, the area of the red fluorescence, and the signal waveform peak value of the side red fluorescence) using the relevant data through the signal processing circuit 4 serving as a characteristic parameter calculation unit, to be described later, (step S204).

In step S205, the necessity of retrieving the waveform data and the characteristic parameter, as well as the necessity of capturing the cell image associated with the waveform data are determined using the characteristic parameter acquired in step S204 by the microprocessor 20 of the measurement control unit 16. In the present embodiment, the image of the cell contained in the measurement sample flowing through the flow cell 51, the waveform data that changes according to the light receiving amount of the light such as the forward scattered light from the cell, and the characteristic parameter calculated from the waveform signal of the light such as the forward scattered light are saved in the storage unit 21 of the apparatus in synchronization. In determining the cancerous cell, the size of the cell is generally small and the DNA amount in the nucleus is greater than the normal cell in the cancerous cell. Thus, in the present embodiment, the microprocessor 20 serving as a determination unit, to be described later, determines in step S205 that the retrieval of the waveform data and the characteristic parameter, as well as the capturing of the cell image are necessary for the cell in the following range using the pulse width of the forward scattered light (FSCW) and the area of the red fluorescence (RFLA) of the characteristic parameters acquired in step S204. In other words, the microprocessor 20 serving as the determination unit determines that the retrieval of the waveform data and the characteristic parameter, as well as the capturing of the cell image are necessary for the cell in a range in which the size of the cell is greater than or equal to 10 μm and smaller than or equal to 50 μm for the range of the FSCW and in a range greater than two times the DNA amount of the normal cell for the range of the RFLA.

Figure 7:
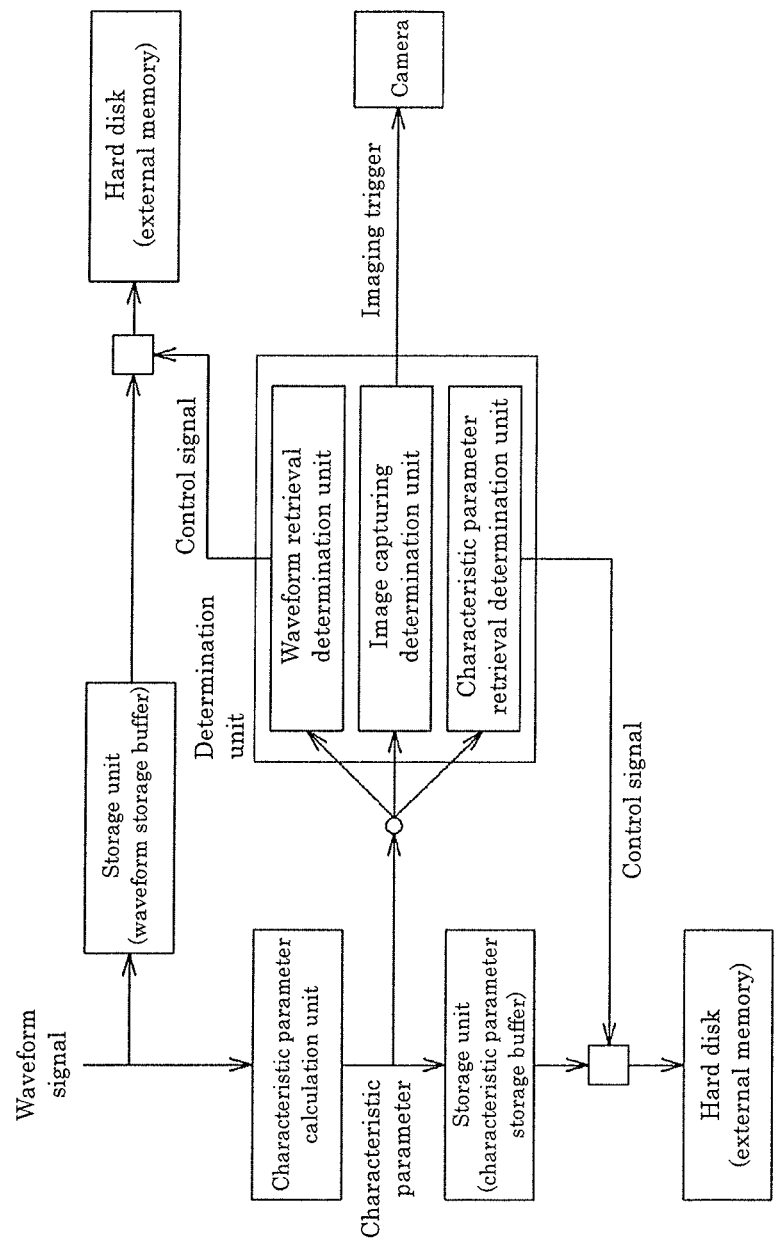
FIG. 7 is a diagram describing a mechanism for synchronizing the waveform and the image.

FIG. 7 is a diagram describing a configuration of synchronizing the capturing of the cell image and the retrieval of the waveform data and the characteristic parameter.

Each waveform data of the forward scattered light, the side scattered light, and the side fluorescence after signal processing such as filtering process and A/D conversion process in the signal processing circuit 4 is temporarily stored in the storage unit 21 serving as the waveform storage buffer, and the characteristic parameter indicating the characteristic of the waveform is calculated in the signal processing circuit 4 serving as the characteristic parameter calculation unit.

Specifically, the pulse width of the forward scattered light (FSCW) and the area of the red fluorescence (RFLA) calculated based on the waveform signal are temporarily stored in the storage unit 21 serving as the characteristic parameter storage buffer, and are used to determine whether or not to retrieve the waveform data and the characteristic parameter as well as whether or not to capture the image of the cell associated with the waveform data and the characteristic parameter in the microprocessor 20 serving as the determination unit. The determination unit includes a waveform retrieval determination unit, an image capturing determination unit, and a characteristic parameter retrieval determination unit.

Returning back to FIG. 6, when it is determined that the retrieval of the waveform data and the characteristic parameter, as well as the capturing of the cell image are necessary for the cell by the microprocessor 20 serving as the determination unit in step S205, the characteristic parameter temporarily stored in the storage unit 21 serving as the characteristic parameter storage buffer is transmitted to the system control unit 13 through the external communication controller 25 by a control signal from the characteristic parameter retrieval determination unit in the subsequent step S206. In this case, the characteristic parameter of the cell determined to be discriminated or analyzed by the determination unit in step S205 is transmitted together with a management number. The waveform data temporarily stored in the storage unit 21 serving as the waveform storage buffer is transmitted to the system control unit 13 through the external communication controller 25 by the control signal from the waveform retrieval determination unit. In this case, the waveform data of the cell determined to be discriminated or analyzed by the determination unit in step S205 is transmitted together with a management number.

The CPU 27a of the system control unit 13 determines whether or not the waveform data and the characteristic parameter are received from the apparatus main body 12 (step S104), and stores the waveform data and the characteristic parameter, which are given management number, in the waveform data storage unit 271d of the hard disk 27d (step S105) if the waveform data and the characteristic parameter are received (YES).

If determined that the retrieval of the waveform data and the characteristic parameter, as well as the capturing of the cell image are necessary (YES) for the cell by the microprocessor 20 serving as the determination unit in step S205, the capturing process is carried out in step S207 in parallel with step S206. When the image capturing determination unit determines that the capturing of the cell image is necessary, the image capturing determination unit sends an imaging trigger signal to the imaging unit 26 to perform the capturing process. When the imaging trigger signal is sent to the imaging unit 26, the pulse laser 66 emits light, and the image of the cell in the flow cell 51 is retrieved by the camera 65 using the illumination by such light emission.

The image data of the captured cell is then transmitted to the system control unit 13 through the external communication controller 25 in step S208. In this case, the image data of the captured cell is transmitted together with a management number in step S208.

The control signals in step S206 and the imaging trigger in step S207 are synchronized, and thus the characteristic parameter, the waveform data, and the cell image saved in the hard disk 27d are guaranteed to be the data of the same cell. Specifically, the management number given to the characteristic parameter and the management number given to the waveform data in step S206, and the management number given to the image of the cell in step S207 are the same number.

The CPU 27a of the system control unit 13 then determines whether or not the image data is received from the apparatus main body 12 (step S106), and stores the image data given the management number in the cell image storage unit 272d of the hard disk 27d (step S107) if the image data is received (YES).

The microprocessor 20 of the apparatus main body 12 carries out the determination on whether or not the flow of sample in the flow cell 51 is finished (step S209), and proceeds the process to step S210 if determined that the flow of sample is finished (YES), and transmits a termination signal to the system control unit 13 in step S210.

The CPU 27a of the system control unit 13 then performs a determination on whether or not the termination signal of the sample flow of the flow cell 51 is received in step S108, and terminates the cell analyzing process if determined that the termination signal is received (YES).

[Display Process]

Figure 8:
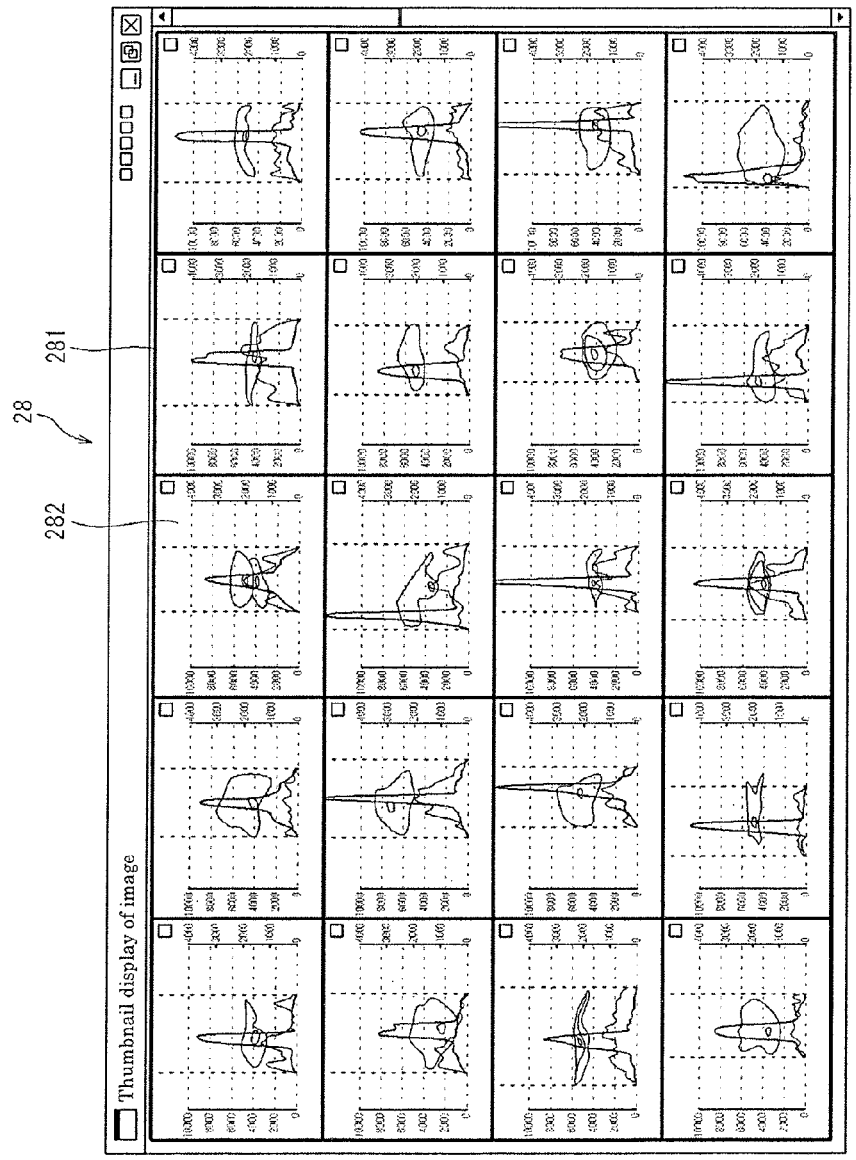
FIG. 8 is a view showing an image example displaying in a list a set of a plurality of captured images, waveform data, and marker.

In the present embodiment, when the user clicks a list display button of a measurement result screen (not shown) after the cell analyzing process is terminated, the CPU 27a of the system control unit 13 performs the display process of displaying a list display screen 281 on the display unit 28. FIG. 8 is the list display screen 281 according to the present embodiment. In the list display screen 281, a plurality of images 282, in which the image of the cell and the graph of the waveform representing the waveform data as well as the marker corresponding to the image of the cell form a set, are displayed in a list. Specifically, in the list display screen 281, a total of 20, four vertical rows and five horizontal columns, images 282, in which the cell image and the graph of the waveform representing the waveform data as well as the marker form a set, are displayed in a list on one screen. Thus, the efficiency of the cell discriminating task can be enhanced by displaying the plurality of images 282 on one screen. The display unit 28 displays each waveform data of the forward scattered light data (FSC), the side scattered light data (SSC), the side red fluorescence data (SRFL), and the side green fluorescence data (SGFL) in a form of a graph showing the waveform.

Figure 9:
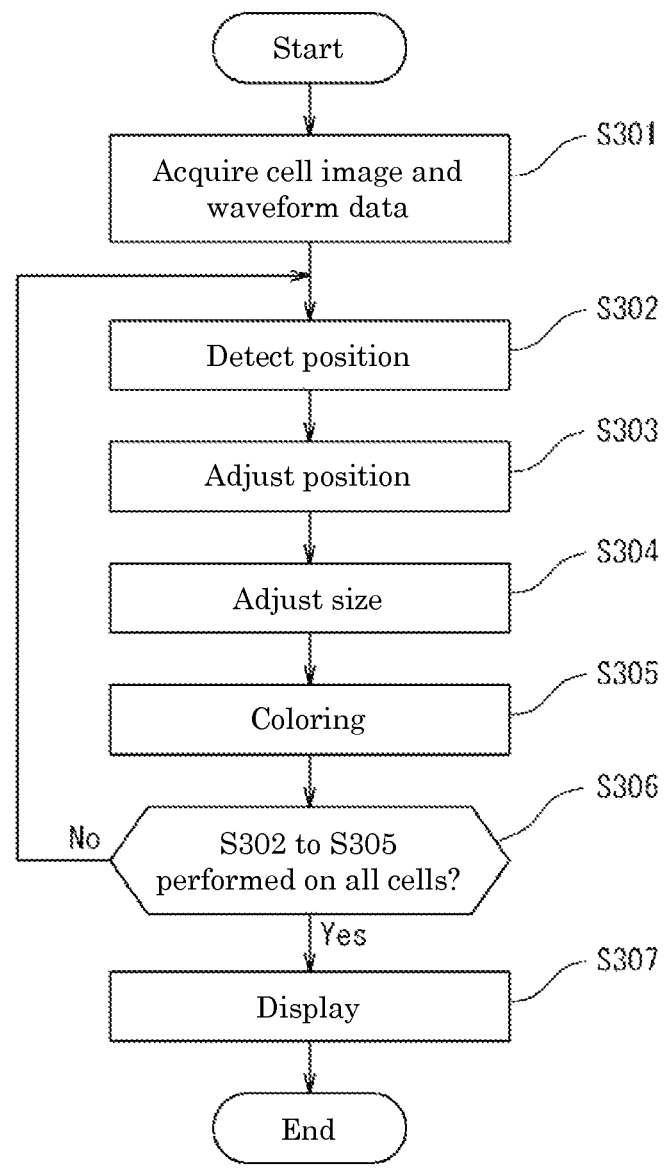
FIG. 9 is a flowchart showing a process at the time of displaying a list display screen shown in FIG. 8.

FIG. 9 is a processing flow in a case where the CPU 27a of the system control unit 13 displays the list display screen 281 shown in FIG. 8 on the display unit 28. In the present embodiment, the image 282, in which the image of the cell and the graph of the waveform representing the waveform data corresponding thereto form a set, is displayed on the display unit 28. In such display, the positions of the cell image and the graph of the waveform representing the waveform data are aligned to facilitate the observation, and the size is adjusted so that the sizes become the same.

When the user clicks the list display button of the measurement result screen (not shown), the CPU 27a of the system control unit 13 acquires all the cell images and waveform data stored in the hard disk 27d (step S301).

The CPU 27a of the system control unit 13 then carries out position detection, to be described later, for the cell image given a predetermined management number n (step S302).

<Position Detection>

In the present embodiment, when displaying the cell image and the graph of the waveform representing the waveform data on the same image, the positions of the cell image and the graph of the waveform representing the waveform data are aligned to facilitate the observation by the operator. In order to align the positions, the CPU 27a of the system control unit 13 executes the position detection process of detecting the position of the cell in the cell image given the management number n in step S302 in the present embodiment.

Figure 10:
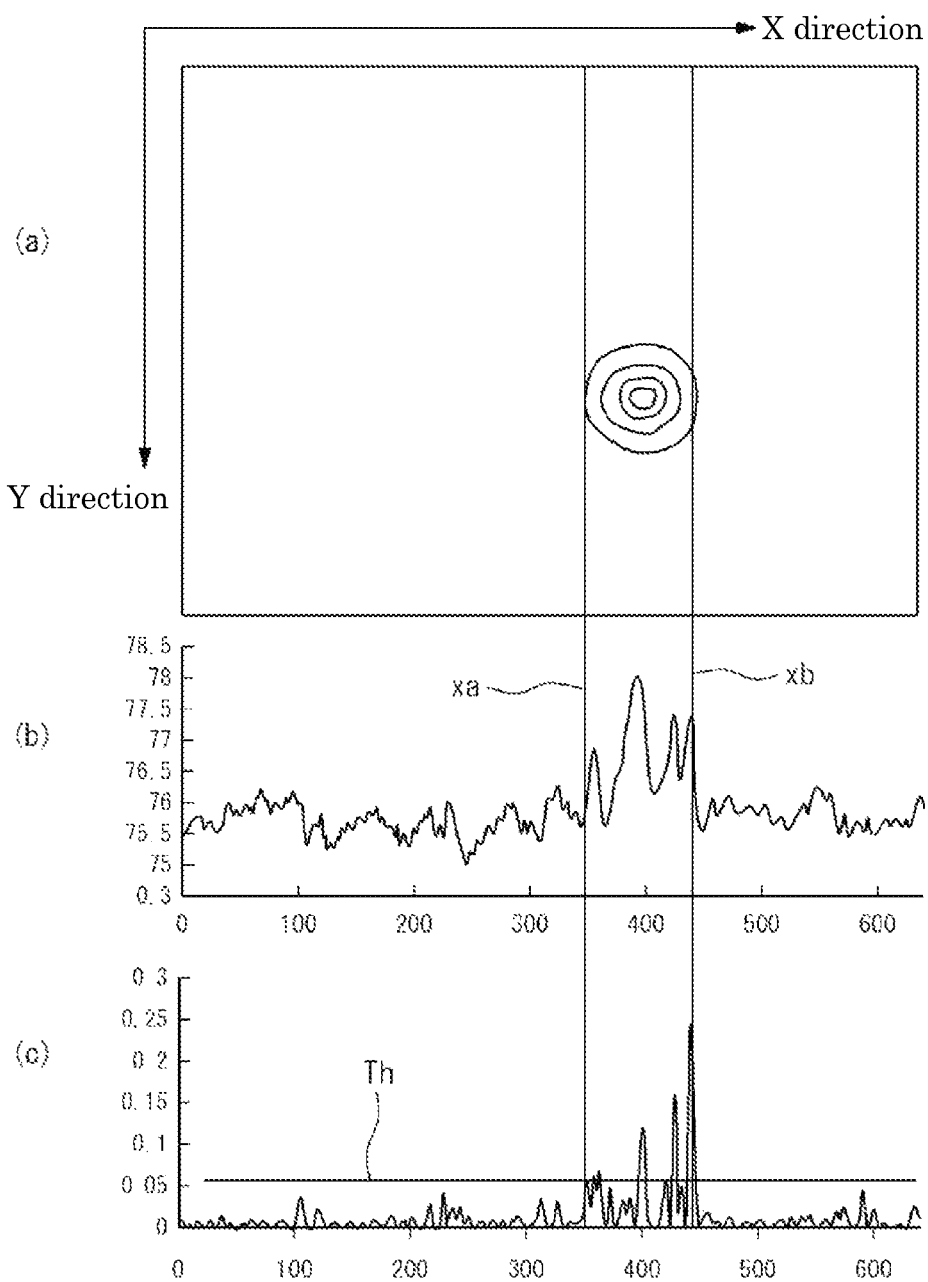
FIG. 10 is a diagram describing a method for detecting a position of a cell in a cell image.

FIG. 10 is a diagram describing a method for the CPU 27a of the system control unit 13 to detect the position of the cell in the cell image in step S302. FIG. 10(a) shows the cell image in which the cell in the flow cell 51 is captured by the camera 65 by emitting light from the pulse laser 66 and using the illumination by the light emission. FIG. 10(b) is a graph showing the change in the X axis direction of an average luminance obtained by adding the luminance of 480 pixels in the Y direction and dividing the sum of the added luminance values by the number (480) of pixels. FIG. 10(c) is a graph showing the change in the X axis direction of a variance value calculated from the average luminance. The position and the size in the X direction of FIG. 10(b) and FIG. 10(c) are drawn to be lined vertically in accordance with the position and the size in the X direction of the image shown in FIG. 10(a). With the upper left corner of the rectangular shaped cell image as the origin, a coordinate having the left and right direction as the X axis and the up and down direction as the Y axis is assumed. First, the luminance values of the image are added in the Y direction, and then averaged. Specifically, assuming the height (Y direction) and the width (X direction) of the image shown in FIG. 10(a) are 480 pixels and 640 pixels, respectively, and the luminance of the coordinate (x, y) is k(x, y), the sum of the luminance values in the Y direction can be calculated along the X direction according to the following equation (1).

[Equation 1]

$$\text{sum}(x) = \sum_{y=1}^{480} k(x, y), \{x: 1 \leq x \leq 640\} \quad (1)$$

First, assuming the average luminance is f(x), the average luminance along the X direction can be obtained with the following equation (2).

[Equation 2]

$$f(x) = \text{sum}(x)/480, [x: 1 \leq x \leq 640] \quad (2)$$

FIG. 10(b) is a graph showing the change in the X axis direction of an average luminance obtained by adding the luminance of 480 pixels in the Y direction and dividing the sum of the added luminance values by the number (480) of pixels.

The variance value is then calculated from the average luminance. FIG. 10(c) is a graph showing the change in the X axis direction of a variance value calculated from the average luminance. As shown in FIG. 10(c), the difference of the position where the cell exists in the image and the position where the cell does not exist can be easily distinguished in the graph showing the change in the X axis direction of the variance value of the average luminance than in the graph showing the change in the X axis direction of the average luminance shown in FIG. 10(b). In the present embodiment, the calculated variance value is used for detecting the position of the cell in the cell image.

A range in which the calculated variance value exceeds a predetermined threshold value (0.05 in the example shown in FIG. 10(c)) is assumed as the position of the cell. The predetermined threshold value Th can be obtained in advance by capturing a sample cell which size is known. In the example shown in FIG. 10, the cell is assumed to be positioned in a range defined by line segments xa and xb parallel to the Y axis. Specifically, the cell is positioned in the range of about 345≤x≤about 440 in the coordinate system assumed as above.

<Position Adjustment>

Figure 11:
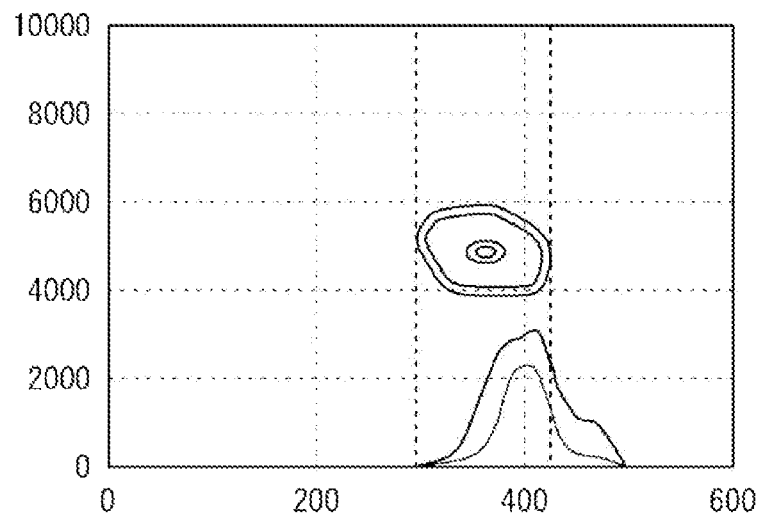
FIG. 11 is a diagram describing an example of a method for aligning the positions and aligning the sizes of the cell image and the waveform data.
Figure 11:
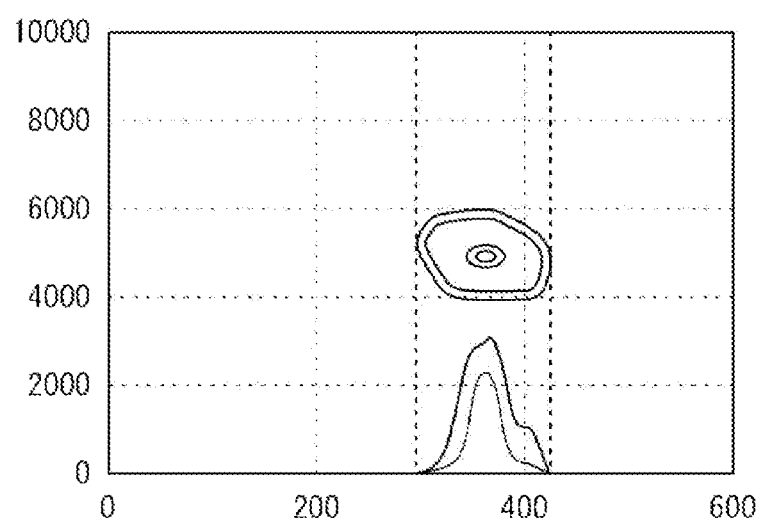

After the position detection is carried out for the cell image given the management number n in step S302, the CPU 27a of the system control unit 13 then executes the process (position adjustment process) of aligning the position of the cell detected in the above manner and the position of the graph of the waveform representing the waveform data associated with the cell (waveform generated from the waveform data of management number n acquired in step S301) (step S303). FIG. 11(a) is a view describing a method in which the CPU 27a of the system control unit 13 aligns the positions of the cell image and the graph of the waveform representing the waveform data in step S303.

As a premise for position alignment, the graph of the waveform representing the waveform data is also displayed in the xy coordinate system, similar to the cell image, where the value of the y coordinate corresponds to the light receiving amount (signal intensity) of the forward scattered light, and the like. Therefore, the graph of the waveform representing the waveform data shows a change that starts from the origin (value of y coordinate is zero) and ends when the value of y coordinate is zero.

Thus, in the present embodiment, the position on the left side of the cell in the cell image (position indicated with the line segment xa in the example shown in FIG. 10) and the origin of the graph of the waveform representing the waveform data associated with the cell are aligned. Thus, the position of the cell and the position of the graph of the waveform representing the waveform data can be adjusted so as to correspond with each other in the left and right direction in the display unit.

<Size Adjustment>

According to the position adjustment described above, the left position of the cell and the origin of the graph of the waveform representing the waveform data can be coincided, but the cell width in the cell image and the signal width of the graph of the waveform representing the waveform data may not necessarily be coincided. Thus, the right position of the cell image and the terminating point (position where the value of the y coordinate becomes zero) of the graph of the waveform representing the waveform data may not be coincided.

Thus, after the position alignment of the cell image given the management number n and the graph of the waveform representing the waveform data is executed in step S303, the CPU 27a of the system control unit 13 executes a size adjustment process of adjusting (enlarging or reducing) the signal width of the forward scattered light so that the size in the x axis direction of the graph of the waveform representing the waveform data of the forward scattered light, for example, of various types of light coincides with the cell width (step S304). Specifically, as shown in FIG. 11(b), the value of the x coordinate is corrected such that the value of the x coordinate where the value of the y coordinate of the graph of the waveform representing the waveform data of the forward scattered light ends at zero, which is shown with a thicker solid line, coincides with the position where the line segment xb intersects with the X axis. Thus, the width of the graph of the waveform representing the waveform data and the cell width can be coincided.

In the present embodiment, the position and the size of the cell image and the graph of the waveform representing the waveform data are adjusted, and the color serving as a marker indicating the characteristic of the waveform data is displayed in an overlapping manner on the cell image and the waveform data. That is, after the size adjustment of the cell image given the management number n and the graph of the waveform representing the waveform data is carried out in step S304, the CPU 27a of the system control unit 13 carries out a coloring process of displaying, in an overlapping manner, the color serving as the marker indicating the characteristic of the waveform data on the cell image given the management number n and the graph of the waveform representing the waveform data (step S305). In the present embodiment, the characteristic of the waveform data shown with the color serving as the marker reflects the size in the x axis direction of the graph of the waveform representing the waveform data, and the size (signal intensity of the waveform data) in the y axis direction of the graph of the waveform representing the waveform data. A correspondence table of the signal intensity (y=f(x)) of the waveform data and the density of the color corresponding thereto is stored in the hard disk 27d. The CPU 27a of the system control unit 13 displays, in an overlapping manner, the color serving as the marker indicating the characteristic of the waveform data on the cell image and the graph of the waveform representing the waveform data based on the correspondence table in step S305.

The CPU 27a of the system control unit 13 then determines whether or not the processes of step S302 to step S305 are executed for all the cell images and waveform data acquired in step S301 (step S306). If determined in step S306 that the processes of step S302 to step S305 are not executed on all the cell images and waveform data acquired in step S301, the CPU 27a of the system control unit 13 returns the process to step S302, and executes the processes of step S302 to step S305 for the management number not yet executed. If determined in step S306 that the processes of step S302 to step S305 are executed on all the cell images and waveform data acquired in step S301, the CPU 27a of the system control unit 13 displays the list display screen 281 shown in FIG. 8 on the display unit 28 (step S307), and terminates the process.

Figure 12:
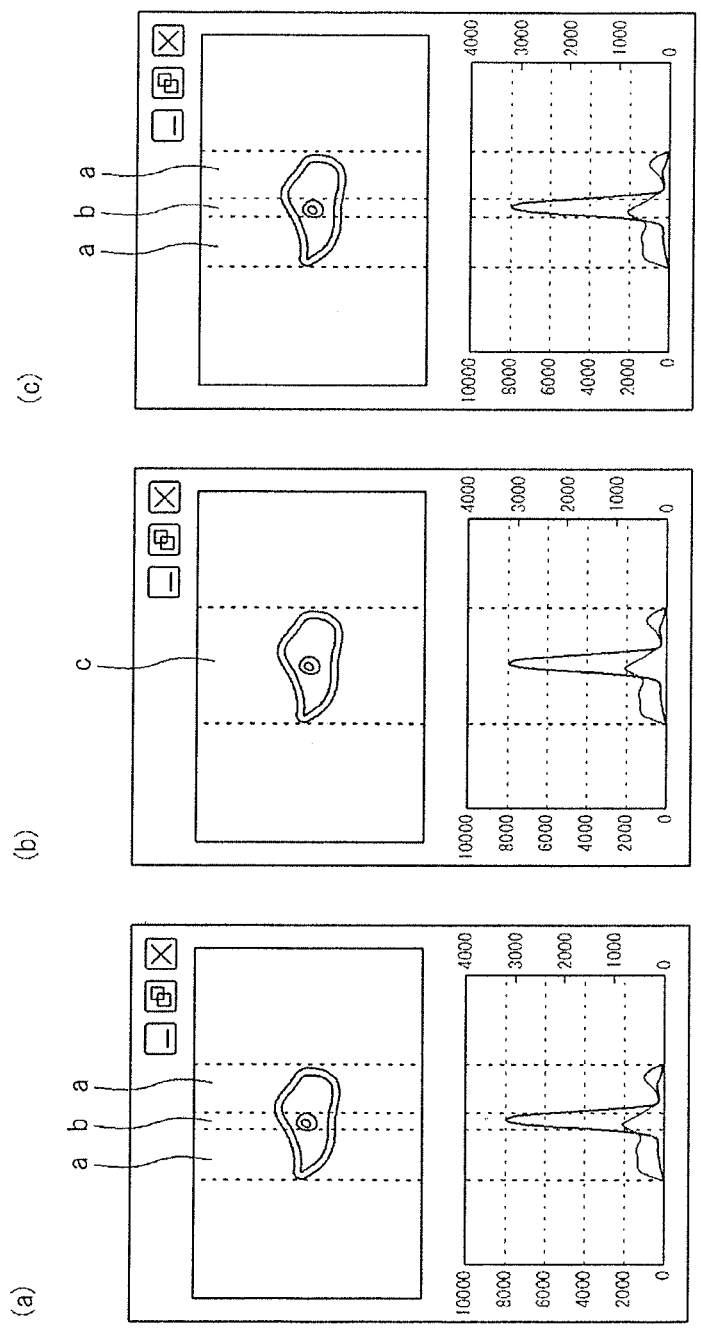
FIG. 12 is a view showing an image example in which two markers are displayed in an overlapping manner.

When one image 282 is selected from the list display screen 281 among the total of 20 images 282, in which the cell image and the graph of the waveform representing the waveform data as well as the marker form a set, a screen including the set of the cell image and the graph of the waveform representing the waveform data, as well as the marker displayed on the selected image 282 is displayed on the display unit 28. FIG. 12(a), FIG. 12(b), and FIG. 12(c) show one example of a screen display in a case where displaying on the display unit 28 a screen including a set of the cell image and the graph of the waveform representing the waveform data as well as the marker displayed in the image 282 selected from the list display screen 281. FIG. 12(a) is a screen displaying an image in which only a translucent red color indicating the characteristic of the waveform data of the side red fluorescence reflecting the DNA amount of the nucleus of the cell is displayed in an overlapping manner on the cell image and the graph of the waveform representing the waveform data. The translucent red color is displayed in an overlapping manner on the cell image and the graph of the waveform representing the waveform data in accordance with the signal intensity of the side red fluorescence shown with a dark solid line in FIG. 12(a). In this case, gradation for making the red darker in proportion to the magnitude of the signal intensity is performed. Specifically, the region indicated as a, which is surrounded by a thick broken line and a thin broken line, is colored with a light translucent red color, and the region indicated as b, which is surrounded by a thin broken line, having a large signal intensity is colored with a dark translucent red color. As a result, the location of the nucleus including the DNA is colored dark compared to the other regions.

Thus, the location and the size of the nucleus in the cell can be easily discriminated by displaying color in an overlapping manner on the cell image and the graph of the waveform representing the waveform data.

In FIG. 12(a) described above, the translucent color serving as the marker indicating the characteristic of the waveform data of the side red fluorescence is displayed in an overlapping manner on the cell image and the graph of the waveform representing the waveform data, but two or more markers may be simultaneously displayed. FIG. 12(b) and FIG. 12(c) show another example of the image display in step S109. FIG. 12(b) is a screen displaying an image in which only a translucent white color indicating the characteristic of the waveform data of the forward scattered light reflecting the thickness of the cytoplasm is displayed in an overlapping manner on the cell image and the graph of the waveform representing the waveform data. In FIG. 12(b), the region indicated as c, which is surrounded by a thick broken line, is colored with translucent white color. FIG. 12(c) is a screen displaying an image in which the translucent red color indicating the characteristic of the waveform data of the side red fluorescence reflecting the DNA amount in the nucleus of the cell and the translucent white color indicating the characteristic of the waveform data of the forward scattered light reflecting the thickness of the cytoplasm are displayed in an overlapping manner on the cell image and the graph of the waveform representing the waveform data. In FIG. 12(c), the region indicated as a, which is surrounded by the thick broken line and the thin broken line, is colored with the light translucent red color and the translucent white color, and the region indicated as b, which is surrounded by the thin broken line, is colored with the dark translucent red color and translucent white color.

The location and the size of the nucleus (FIG. 12(a)) and the location and the size of the cell (FIG. 12(b)) can be discriminated according to the images of FIG. 12(a) and FIG. 12(b), where the location and the size of the nucleus and the location and the size of the cell can be easily discriminated from one image by displaying, in an overlapping manner, red and white colors simultaneously, as shown in FIG. 12(c).

Figure 13:
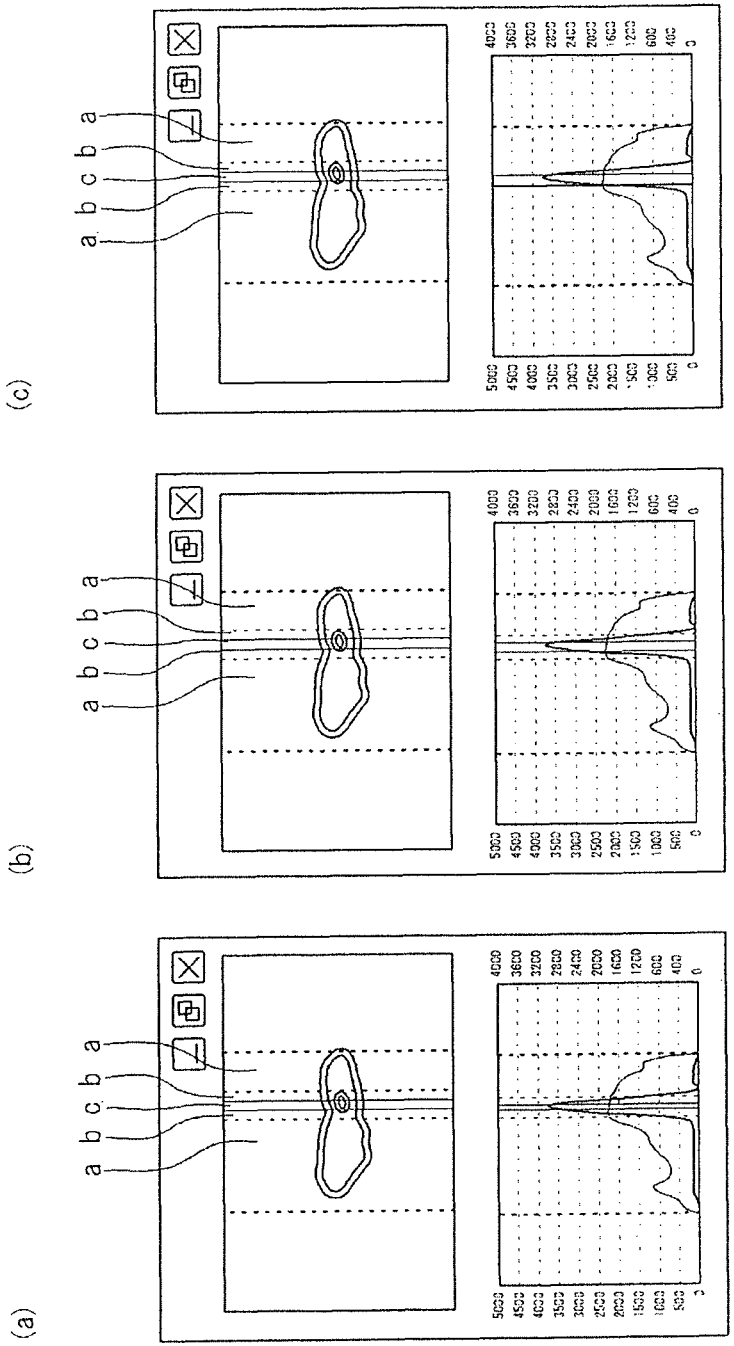
FIG. 13 is a view showing an image example drawn with a color map different from each other.

The coloring corresponding to the signal intensity of the waveform data may be variously changed using the known color mapping technique other than simply changing the density of the color according to the signal intensity (y=f(x)) of the waveform data as shown in FIG. 12(a) and FIG. 12(b). FIG. 13 shows an image example drawn with a color map different from each other. FIGS. 13(a) to 13(c) all show the image of the same cell, but the easiness in recognizing the location and the size of the nucleus of the cell changes by changing the color map. In FIG. 13(a), the region indicated as a, which is surrounded by the thick broken line and the thin broken line, is colored blue, the region indicated as b, which is surrounded by the thin broken line and the thin solid line, is colored yellow, and the region indicated as c, which is surrounded by the thin broken line, is colored red. In FIG. 13(b), the region indicated as a, which is surrounded by the thick broken line and the thin broken line, is colored red, the region indicated as b, which is surrounded by the thin broken line and the thin solid line, is colored yellow, and the region indicated as c, which is surrounded by the thin broken line, is colored blue. In FIG. 13(c), the region indicated as a, which is surrounded by the thick broken line and the thin broken line, is colored gray, the region indicated as b, which is surrounded by the thin broken line and the thin solid line, is colored red, and the region indicated as c, which is surrounded by the thin broken line, is colored yellow.

Thus, the cell discrimination by the operator can be assisted by variously changing the color itself and the extent of change in the shading of the color.

Figure 14:
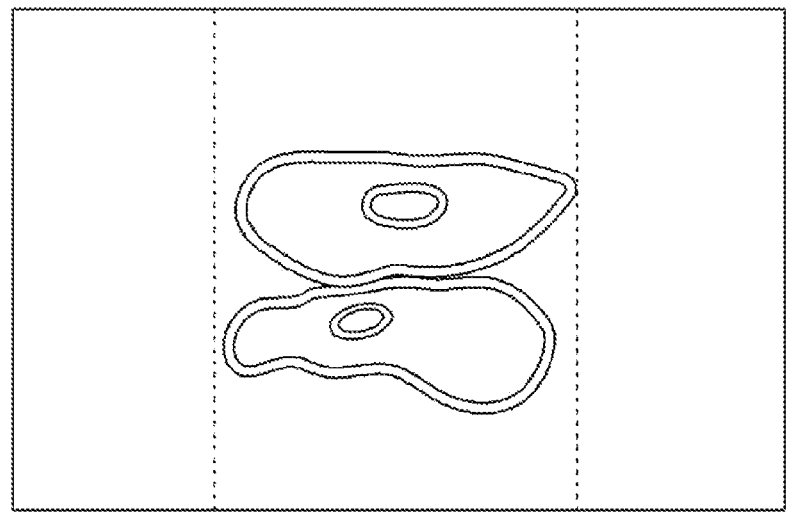
FIG. 14 is a view showing another image display example.
Figure 14:
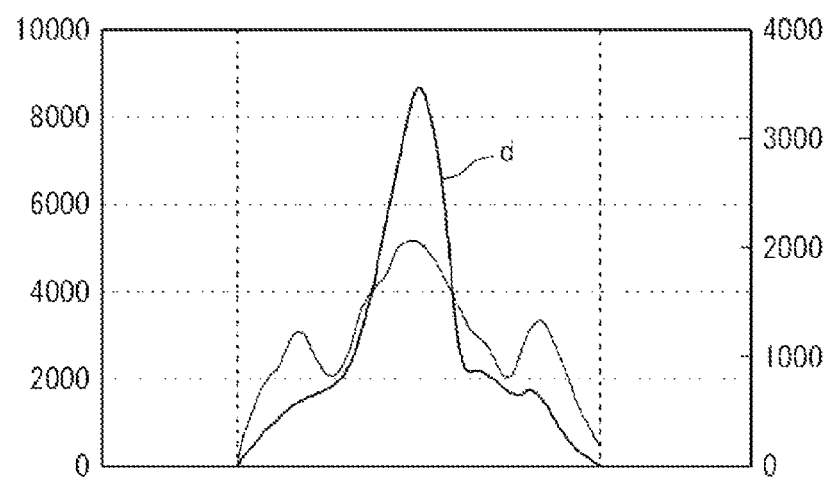

FIG. 14 shows another image display example. In the cell analysis using the flow cell, a procedure for stirring the sample including cells collected from the subject is performed to prevent aggregation of the cells as a preliminary preparation for flowing cells to the flow cell, but the sample flowing through the flow cell infrequently contain aggregated cells. For example, if two cells are overlapped such that the nuclei are at substantially the same position, this may be considered as one cell having great DNA amount since the graph d of the waveform representing the waveform data of the side red fluorescence shows one large single peak, as shown in FIG. 14(b). However, it is easily apparent that two cells are overlapped by looking at the cell image of FIG. 14(a). Thus, even the discrimination of cells that is difficult to recognize with only the graph of the waveform representing the waveform data can be easily carried out at high accuracy by combining the graph of the waveform representing the waveform data and the image.

Figure 15:
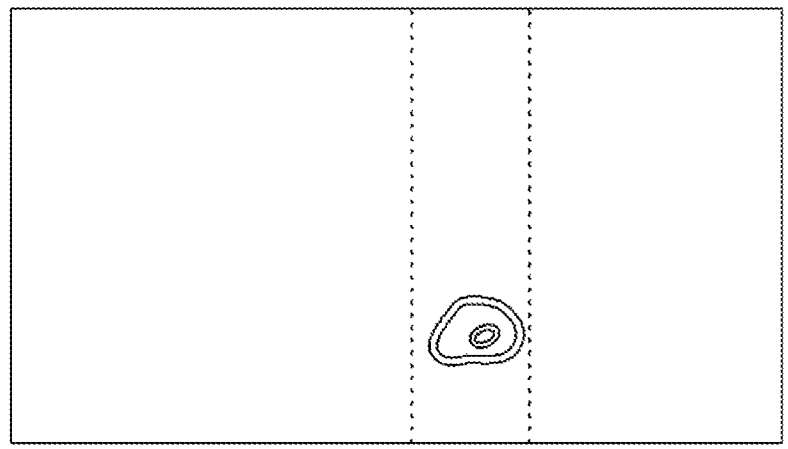
FIG. 15 is a view describing discrimination of a position of a nucleus.
Figure 15:
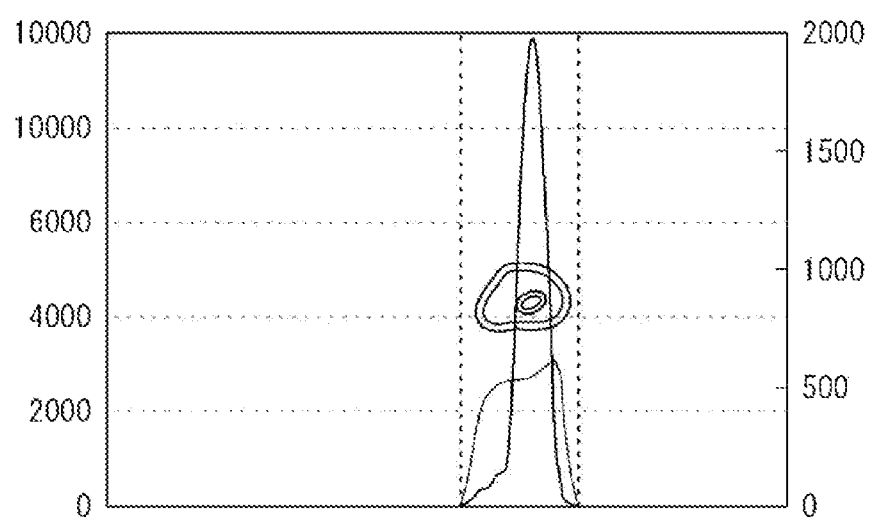

FIG. 15 is a view describing an example in which the position of the nucleus is difficult to determine with only the cell image but the position of the nucleus can be easily determined by combining with the graph of the waveform representing the waveform data. When performing cell analysis using the flow cell, the cell flowing through the center of the flow cell and the cell flowing near the wall surface of the flow cell may be defocused if the cell in the flow cell is photographed with the camera at a predetermined focus. Thus, the image of the photographed cell may be blurred and the position of the nucleus may be difficult to determine as in the cell image of FIG. 15(a). However, the position of the nucleus can be easily recognized by looking at the graph of the waveform representing the waveform data of FIG. 15(b). In FIG. 15(b), the thick solid line is the graph of the waveform representing the waveform data of the side red fluorescence. Thus, even the discrimination of cells that is difficult to recognize with only the cell image can be easily carried out at high accuracy by combining the graph of the waveform representing the waveform data and the image.

[Other Variants]

The embodiment disclosed herein is merely illustrative in all aspects and should not be recognized as being exclusive. The scope of the invention is defined by the scope of the claims rather than by the description of the embodiment, and meaning equivalent to the claims and all modifications within the scope are encompassed herein.

For example, in the embodiment described above, a case of displaying in a list a set of a plurality of cell images and the graph of the waveform representing the waveform data of the cell as well as the color serving as the marker indicating the characteristics of the waveform data has been described, but a set of one cell image and the graph of the waveform representing the waveform data as well as the marker may be displayed on the display unit, as shown in FIG. 12(a), FIG. 12(b), and FIG. 12(c).

In the embodiment described above, the cell image and the graph of the waveform representing the waveform data as well as the marker are displayed on the same screen, but the cell image and the graph of the waveform representing the waveform data as well as the marker may be displayed on different screens. Although discrimination can be made while comparing by displaying the cell image and the like on the same screen, the cell image and the like can advantageously be displayed large if displayed separately.

Furthermore, in the embodiment described above, the position adjustment of the cell image and the graph of the waveform representing the waveform data is carried out by shifting the graph of the waveform representing the waveform data, but the position adjustment of the cell image and the graph of the waveform representing the waveform data may be carried out by shifting the cell image.

Furthermore, in the embodiment described above, the size adjustment of the cell image and the graph of the waveform representing the waveform data is carried out by enlarging or reducing the width of the graph of the waveform representing the waveform data, but the size adjustment of the cell image and the graph of the waveform representing the waveform data may be carried out by enlarging or reducing the cell image.

In the embodiment described above, the cell image, the graph of the waveform representing the waveform data, and the color serving as the marker indicating the characteristic of the waveform data are displayed on one screen, but only one of the graph of the waveform representing the waveform data and the marker may be displayed.

In the embodiment described above, color is illustrated as the marker indicating the characteristic of the waveform data, but a schematic view of the cell represented by a circular figure, for example, may be used as the marker other than the color. Specifically, a first circle is drawn with the forward scattered light intensity representing the size of the cell as a radius, and a second circle is drawn concentric with the first circle with a fluorescence intensity representing the size of the nucleus of the cell as a radius, so that a double circle like the schematic view of the cell can be drawn. This can be displayed as the marker indicating the characteristic of the waveform data to be displayed with the cell image.

In the embodiment described above, whether or not the cancerous/atypical cell of the uterine cervix exists in the measurement sample collected from the subject is determined, but the cell analyzer of the present invention is not limited thereto, and may be used to determine whether or not a predetermined number or more of the cancerous/atypical cells of the buccal cell and other epidermal cells such as bladder and pharynges, and furthermore, the cancerous/atypical cells of organs exist in the measurement sample collected from the subject.

In the embodiment described above, the configuration in which one hard disk 27*d* includes the waveform data storage unit 271*d* for storing the waveform data and the cell image storage unit 272*d* for storing the cell image has been described, but the present invention is not limited thereto. The waveform data storage unit 271*d* and the cell image storage unit 272*d* may be configured by different storage devices.

Furthermore, in the embodiment described above, the configuration in which the color is gradated according to the intensity of the fluorescence signal for the characteristic of the waveform data capable of reflecting the position of the nucleus of the cell has been described, but the present invention is not limited thereto. The present invention may have a configuration in which the color is displayed in a range in which the intensity of the fluorescence signal is greater than or equal to a predetermined value for the characteristic of the waveform data capable of reflecting the position of the nucleus of the cell.

Moreover, in the embodiment described above, the configuration in which the color is gradated according to the intensity of the scattered light signal for the characteristic of the waveform data capable of reflecting the thickness of the cytoplasm (size of the cell) has been described, but the present invention is not limited thereto. The present invention may have a configuration in which the color is displayed in a range in which the intensity of the scattered light signal is greater than or equal to a predetermined value for the characteristic of the waveform data capable of reflecting the size of the cell.

In the embodiment described above, the configuration in which the graph representing the waveform of the data is displayed in a form of a line graph has been described, but the present invention is not limited thereto. The present invention may display the graph representing the waveform of the data in a form of a histogram.

What is claimed is:

1. A cell analyzer comprising:
    a flow cell through which a sample containing a cell flows, the cell including a stained nucleus;
    an imaging unit configured to capture the cell contained in the sample flowing through the flow cell;
    a light source configured to irradiate the sample flowing through the flow cell with light;
    a light receiving unit configured to receive flourescence from the cell irradiated with the light from the light source and outputs a signal corresponding to amount of the received fluorescence;
    a memory configured to store a cell image captured by the imaging unit in association with fluorescence waveform data indicating change in the amount of the received fluorescence obtained based on the output signal;
    a display unit; and
    a processor programmed to
        control the display unit to display the cell image aligned with and overlapped with a graph representing the fluorescence waveform data corresponding to an amount of genetic material represented for the cell in the cell image, so that sizes and positions of the cell image, an intensity of the fluorescence, and the graph are correlated, and
        execute a size adjustment process such that a cell width in the cell image and a width of the graph coincide with each other.

2. The cell analyzer according to claim 1, wherein the processor is further programmed to control the display unit to display the cell image and the graph on the same screen.

3. The cell analyzer according to claim 2, wherein the processor is further programmed to execute position adjustment of adjusting a position of one of the cell image and the graph according to a position of the other one, and controls the display unit to display the cell image and the graph after the position adjustment.

4. The cell analyzer according to claim 1, wherein the processor is further programmed to execute size adjustment of adjusting a size of one of the cell image and the graph according to a size of the other one, and controls the display unit to display the cell image and the graph after the size adjustment.

5. The cell analyzer according to claim 1, wherein the processor is further programmed to control the display unit to display a set of the cell image and the graph in a list.

6. The cell analyzer according to claim 1, wherein the processor is further programmed to control the display unit to display a color displayed with a density corresponding to the light receiving amount.

7. The cell analyzer according to claim 6, wherein the waveform data includes data indicating temporal change of a fluorescence intensity for a predetermined cell; and
    the processor is further programmed to control the display unit to display the color displayed with a density corresponding to the fluorescence intensity.

8. The cell analyzer according to claim 6, wherein the waveform data includes data indicating temporal change of a scattered light intensity for a predetermined cell; and
the processor is further programmed to control the display unit to display the color displayed with a density corresponding to the scattered light intensity.

9. The cell analyzer according to claim 1, wherein the waveform data includes data indicating temporal change of a fluorescence intensity for a predetermined cell; and
the processor is further programmed to control the display unit to display a color given to a range in which the fluorescence intensity is greater than or equal to a predetermined value.

10. The cell analyzer according to claim 9, wherein the processor is further programmed to control the display unit to display the range in which the fluorescence intensity is greater than or equal to the predetermined value as information reflecting a position of a nucleus in the predetermined cell.

11. The cell analyzer according to claim 1, wherein the waveform data includes data indicating temporal change of a scattered light intensity for a predetermined cell; and
the processor is further programmed configured to control the display unit to display a color given to a range in which the scattered light intensity is greater than or equal to a predetermined value.

12. The cell analyzer according to claim 11, wherein the processor is further programmed to control the display unit to display the range in which the scattered light intensity is greater than or equal to the predetermined value is information reflecting a size of the predetermined cell.

13. The cell analyzer according to claim 6, wherein the processor is further programmed to control the display unit to display the color and the cell image in an overlapping manner.

14. The cell analyzer according to claim 13, wherein the processor is further programmed to control the display unit to display a plurality of colors in an overlapping manner.

15. The cell analyzer according to claim 3, wherein the processor is further programmed to execute size adjustment of adjusting a size of one of the cell image and the graph according to a size of the other one, and to control the display unit to display the cell image and the graph after the size adjustment.

16. The cell analyzer according to claim 1, further comprising:
a first photomultiplier tube configured to detect side red fluorescence data (SRFL) divided from a side fluorescence transmitted from a first dichroic mirror through a second dichroic minor; and
a second photomultiplier tube, different than the first photomultiplier tube, configured to detect side green fluorescence data (SGFL) divided from the side fluorescence.

17. The cell analyzer according to claim 1, wherein the processor is further programmed to control the display unit to display the cell image aligned with the graph at same sizes thereof such that an axial pixel length of the cell image is equal to a pixel length of the graph in a same axial direction, wherein
the graph is aligned with a nucleus of the cell.

* * * * *